US010524682B2

(12) United States Patent
Garcia Molina et al.

(10) Patent No.: US 10,524,682 B2
(45) Date of Patent: Jan. 7, 2020

(54) SYSTEM AND METHOD FOR DETERMINING AND DISPLAYING SLEEP RESTORATION LEVELS

(71) Applicant: KONINKLIJKE PHILIPS N.V., Eindhoven (NL)

(72) Inventors: Gary Nelson Garcia Molina, Madison, WI (US); Manuel Laura Lapoint, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 294 days.

(21) Appl. No.: 15/319,091

(22) PCT Filed: Jun. 25, 2015

(86) PCT No.: PCT/IB2015/054756
§ 371 (c)(1),
(2) Date: Dec. 15, 2016

(87) PCT Pub. No.: WO2016/001800
PCT Pub. Date: Jan. 7, 2016

(65) Prior Publication Data
US 2017/0127967 A1 May 11, 2017

Related U.S. Application Data

(60) Provisional application No. 62/020,051, filed on Jul. 2, 2014.

(51) Int. Cl.
A61B 5/00 (2006.01)
A61B 5/0482 (2006.01)
A61B 5/0476 (2006.01)

(52) U.S. Cl.
CPC .......... *A61B 5/0482* (2013.01); *A61B 5/0476* (2013.01); *A61B 5/4806* (2013.01);
(Continued)

(58) Field of Classification Search
USPC ........................................................ 340/575
See application file for complete search history.

(56) References Cited

U.S. PATENT DOCUMENTS

2008/0081941 A1 4/2008 Tononi
2008/0208027 A1 8/2008 Heaton
(Continued)

FOREIGN PATENT DOCUMENTS

JP 2007319238 A 12/2007
JP 2013173043 A 9/2013
WO WO-2014038594 A1 * 3/2014 ........... A61B 5/7435
WO 2014170881 A1 10/2014

OTHER PUBLICATIONS

Borbely, "A Two Process Model of Sleep Regulation", Human Neurobiology, vol. 1, 1982, pp. 195-204.
(Continued)

*Primary Examiner* — Etsub D Berhanu

(57) ABSTRACT

The present disclosure pertains to a system and method for determining and displaying a sleep restoration level of a subject for a target sleep session. In some embodiments, the system comprises one or more of a sensor, a processor, electronic storage, a user interface, and/or other components. As the subject sleeps, the system is configured to determine a metric indicating sleep need for the subject and then graphically display a sleep restoration level (a visual representation of the metric indicating sleep need) based on the determined sleep need metric. Instead of assuming common parameters for multiple users, the system is configured to determine the sleep need metric based on obtained baseline sleep parameters that have been determined individually for the subject based on one or more previous sleep sessions, a determined amount of slow wave activity in the subject during the target sleep session, and/or other information.

12 Claims, 11 Drawing Sheets

(52) U.S. Cl.
CPC ............ *A61B 5/4812* (2013.01); *A61B 5/743* (2013.01); *A61B 5/7475* (2013.01)

(56) References Cited

U.S. PATENT DOCUMENTS

| | | |
|---|---|---|
| 2011/0018720 A1 | 1/2011 | Rai et al. |
| 2015/0127265 A1 | 5/2015 | Iizuka |
| 2015/0150516 A1* | 6/2015 | Tochikubo ............ A61B 5/7435 600/301 |

OTHER PUBLICATIONS

Garcia-Molina et al, "Online Single EEG Channel Based Automatic Sleep Staging", EPCE/HCII, PartII, LNAI 8020, 2013, pp. 333-342.
Achermann et al, "Simulation of Human Sleep: Ultradian Dynamics of Electroencephalographic Slow-Wave Activity", Journal of Biological Rhythms, vol. 5, No. 2, 1990, pp. 141-157.
Dijk et al, "Time Course of EEG Power Density During Long Sleep in Humans", The American Physiological Society, 1990, pp. R650-R661.
Marshall et al, "Use of Personal EEG Monitors in a Behavioral Neuroscience Course to Investigate Natural Setting Sleep Patterns and the Factors Affecting Them in College Students", The Journal of Undergraduate Neuroscience Education, vol. 10, No. 1, 2011, pp. A65-A70.
Achermann et al, "A Model of Human Sleep Homeostasis Based on EEG Slow-Wave Activity: Quantitative Comparison of Data and Simulations", Brain Research Bulletin, vol. 31, 1993, pp. 97-113.

* cited by examiner

SYSTEM AND METHOD FOR DETERMINING AND DISPLAYING SLEEP RESTORATION LEVELS

CROSS-REFERENCE TO PRIOR APPLICATIONS

This application is the U.S. National Phase application under 35 U.S.C. § 371 of International Application Serial No. PCT/IB2015/054756, filed on Jun. 25, 2015, which claims the benefit of U.S. Application Ser. No. 62/020,051, filed on Jul. 2, 2014. These applications are hereby incorporated by reference herein.

BACKGROUND

1. Field

The present disclosure pertains to a system configured to determine and display a sleep restoration level of a subject for a target sleep session.

2. Description of the Related Art

Systems for monitoring sleep are known. These systems may roughly estimate a subject's need for sleep but do not take into account the subjective experience of an individual subject (e.g., an individual's unique brain activity) during a sleep session. For example, some prior art systems indicate sleep need with a single numeric score. The determination of the single numeric score relies on an assumed ideal sleep duration of 8.5 hours for all subjects and that more sleep is always better (which is not always the case for every subject). The present disclosure overcomes deficiencies in prior art systems.

SUMMARY

Accordingly, one or more aspects of the present disclosure relate to a system configured to determine and display a sleep restoration level of a subject for a target sleep session. The system comprises one or more sensors, one or more physical computer processors, and/or other components. The one or more sensors are configured to generate output signals conveying information related to the subject's brain electrical signal power in a slow frequency band (e.g., about 0.5 to about 4.5 Hz which is commonly known as slow wave activity (SWA)) in the subject during the target sleep session. The one or more physical computer processors are configured, by computer readable instructions, to: obtain an initial sleep need amount and a sleep need decay rate determined based on information from one or more previous sleep sessions of the subject; determine an amount of slow wave activity in the subject during the target sleep session based on the output signals; determine a metric indicating sleep need dissipation in the subject during the target sleep session, the metric determined based on the initial sleep need amount, the sleep need decay rate, and the determined amount of slow wave activity; and cause a user interface to graphically display the sleep restoration level of the subject for the target sleep session, the sleep restoration level comprising a visual representation of the metric indicating sleep need dissipation.

Yet another aspect of the present disclosure relates to a method for determining and displaying a sleep restoration level of a subject for a target sleep session with a determination system. The determination system comprises one or more sensors, one or more physical computer processors, and/or other components. The method comprises: generating, with the one or more sensors, output signals conveying information related to slow wave activity in the subject during the target sleep session; obtaining, with the one or more physical computer processors, an initial sleep need amount and a sleep need decay rate determined based on information from one or more previous sleep sessions of the subject; determining, with the one or more physical computer processors, an amount of slow wave activity in the subject during the target sleep session based on the output signals; determining, with the one or more physical computer processors, a metric indicating sleep need dissipation in the subject during the target sleep session, the metric determined based on the initial sleep need amount, the sleep need decay rate, and the determined amount of slow wave activity; and causing, with the one or more physical computer processors, a user interface to graphically display the sleep restoration level of the subject for the target sleep session, the sleep restoration level comprising a visual representation of the metric indicating sleep need dissipation.

Still another aspect of present disclosure relates to a system configured to determine and display a sleep restoration level of a subject for a target sleep session. The system comprises: means for generating output signals conveying information related to slow wave activity in the subject during the target sleep session; means for obtaining an initial sleep need amount and a sleep need decay rate determined based on information from one or more previous sleep sessions of the subject; means for determining an amount of slow wave activity in the subject during the target sleep session based on the output signals; means for determining a metric indicating sleep need dissipation in the subject during the target sleep session, the metric determined based on the initial sleep need amount, the sleep need decay rate, and the determined amount of slow wave activity; and means for causing a user interface to graphically display the sleep restoration level of the subject for the target sleep session, the sleep restoration level comprising a visual representation of the metric indicating sleep need dissipation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
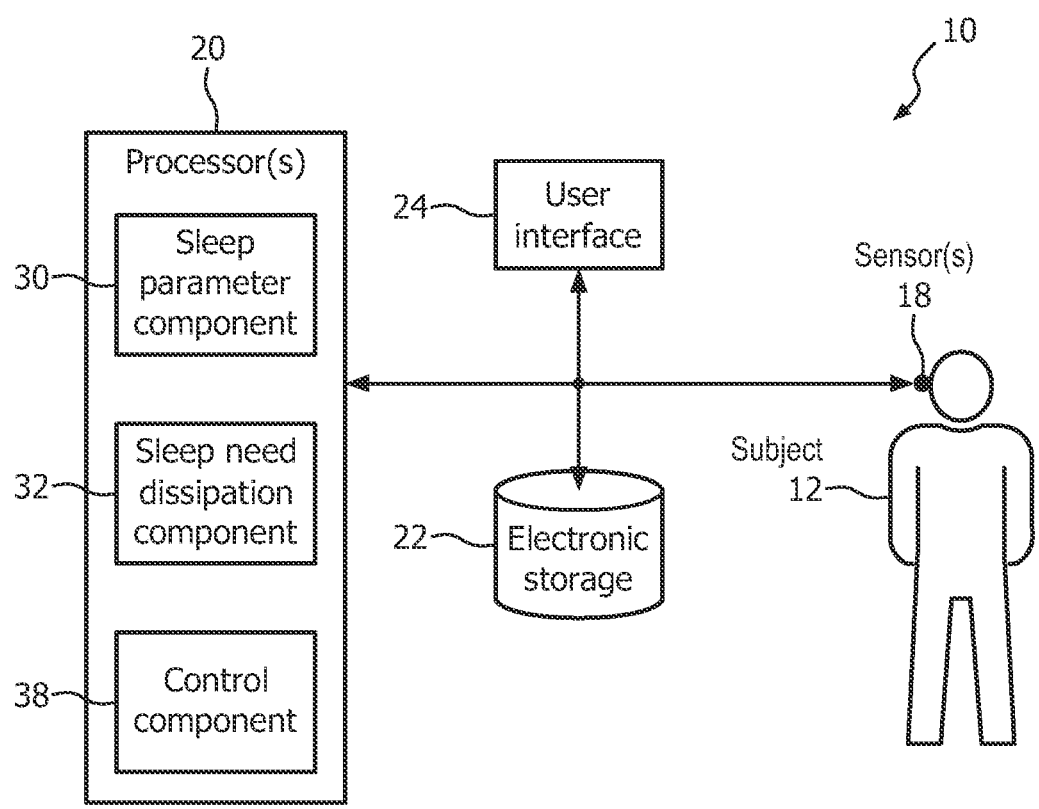
FIG. 1 is a schematic illustration of a system configured to determine and display a sleep restoration level of a subject for a target sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine and display a sleep restoration level of a subject 12 for a target sleep session. The target sleep session may be a current sleep session of the subject (e.g., system 10 may function as described herein while subject 12 is currently sleeping), a previous sleep session of the subject (e.g., system 10 may function as described herein based on data collected during a previous sleep session of subject 12), and/or other sleep sessions. In some embodiments, system 10 may comprise one or more of a sensor 18, a processor 20, electronic storage 22, a user interface 24, and/or other components. As a sleep session progresses, system 10 is configured to determine a metric indicating sleep need for subject 12 and then graphically display a sleep restoration level (a visual representation of the metric indicating sleep need) based on the determined sleep need metric. Instead of assuming common parameters for multiple users, system 10 is configured to determine the sleep need metric based on obtained baseline sleep parameters (e.g., an initial sleep need amount and a sleep need decay rate described below) that have been determined individually for subject 12 based on one or more previous sleep sessions (e.g., previous to the target sleep session) of subject 12, a determined (in real-time or near real-time) amount of slow wave activity in subject 12 during the target sleep session, and/or other information. In FIG. 1, sensor 18, processor 20, electronic storage 22, and user interface 24 are shown as separate entities. This is not intended to be limiting. Some and/or all of the components of system 10 and/or other components may be grouped into one or more singular devices.

Sensor 18 is configured to generate output signals conveying information related to slow wave activity in subject 12, a target sleep stage of subject 12, and/or other information. Sensor 18 is configured to generate output signals before, during, and/or after sleep sessions of subject 12, and/or other users. Slow wave activity (SWA) may be estimated (described below) from an electroencephalogram (EEG) and/or with other methods for subject 12 during a given sleep session. SWA corresponds to the power of the EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next.

SWA is related to sleep need. Sleep need is a user's (e.g., subject 12) need for sleep during a given sleep session. Sleep need builds up during wakefulness and dissipates during sleep. The decrease in SWA throughout a sleep session reflects the dissipation of sleep need. Sleep need dissipates and/or decreases as subject 12 sleeps. The dissipation dynamics depend on the given subject. The manner in which dissipation occurs regulates the duration of a given sleep session and is linked to the temporal dynamics of SWA. SWA may correspond to one or more sleep stages of subject 12. The sleep stages of subject 12 may be and/or correspond to one or more of non-rapid eye movement (NREM) stage N1, stage N2, or stage N3 sleep, and/or rapid eye movement (REM) sleep. In some embodiments, NREM stage 3 or stage 2 sleep may be slow wave sleep. The sleep need declines at a rate proportional to the SWA during NREM sleep.

Figure 2:
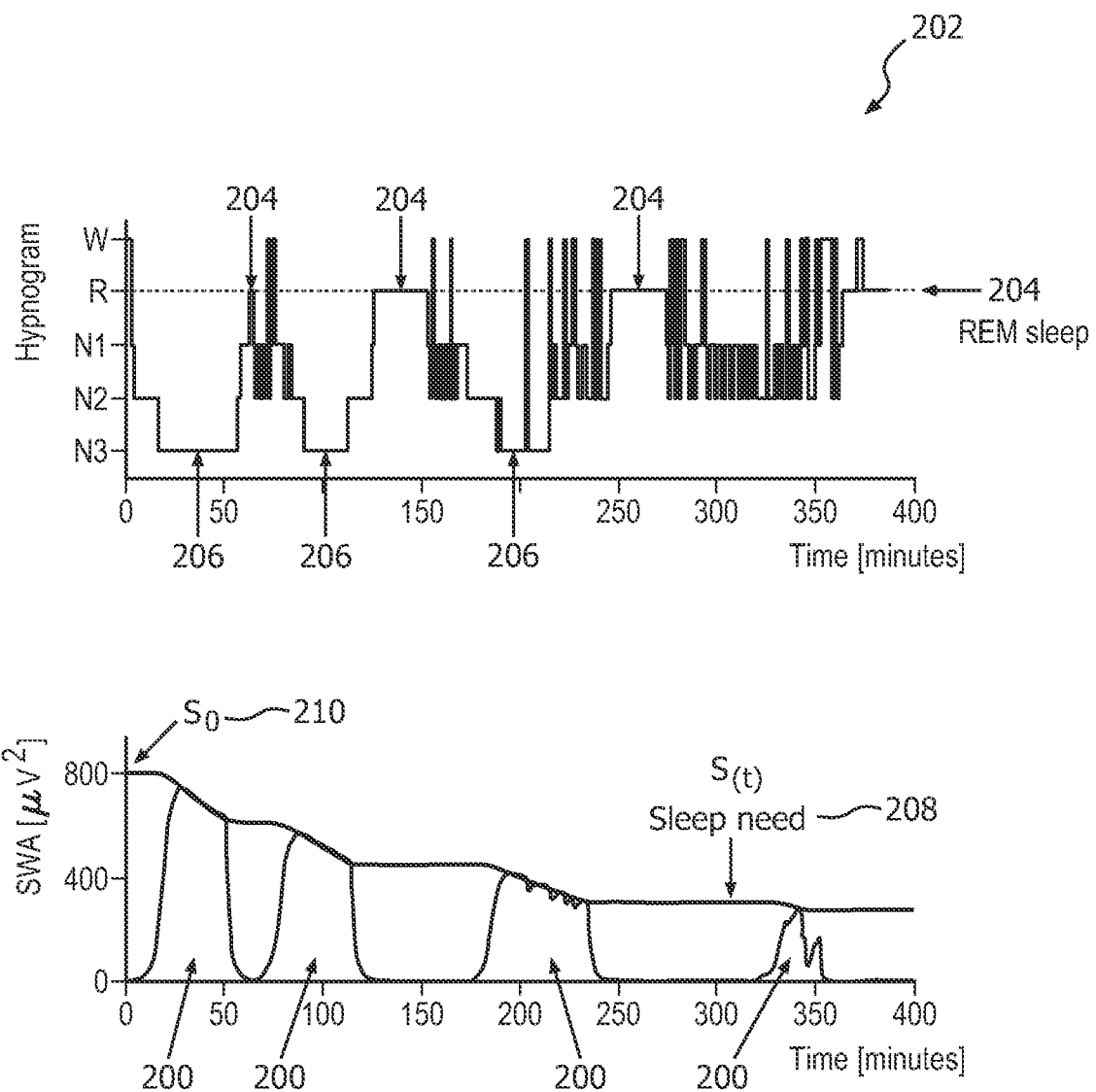
FIG. 2 illustrates slow wave activity, a hypnogram showing REM sleep periods and slow wave sleep periods, and sleep need as a function of time during a sleep session.

For example, FIG. 2 illustrates SWA 200, a hypnogram 202 showing REM sleep periods 204 and slow wave sleep periods 206, and sleep need as a function of time, S(t) 208, during a sleep session. An initial sleep need amount, $S_0$ 210, is also shown in FIG. 2. Sleep need as a function of time, S(t) 208, decreases from initial sleep need amount 210 during the sleep session as the subject sleeps. FIG. 2 illustrates that sleep need as a function of time 208 decreases faster during periods of SWA 200 and/or slow wave sleep 206.

Returning to FIG. 1, sensor 18 may comprise one or more sensors that generate output signals related to such parameters (e.g., slow wave activity, sleep stage, sleep need, etc.) directly. For example, sensor 18 may include electrodes configured to detect electrical activity along the scalp of subject 12 resulting from current flows within the brain of subject 12. Sensor 18 may comprise one or more sensors that generate output signals conveying information related to slow wave activity and/or a sleep stage of the subject indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location in communication with subject 12, this is not intended to be limiting. Sensor 18 may include sensors disposed in a plurality of locations, such as for example, within (or in communication with) processor 20, and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensor 18), or processor 20 may represent processing functionality of a plurality of devices operating in coordination.

As shown in FIG. 1, processor 20 is configured to execute one or more computer program components. The one or more computer program components may comprise one or more of a sleep parameter component 30, a sleep need dissipation component 32, a control component 38, and/or other components. Processor 20 may be configured to execute components 30, 32, and/or 38 by software; hardware; firmware; some combination of software, hardware, and/or firmware; and/or other mechanisms for configuring processing capabilities on processor 20.

It should be appreciated that although components 30, 32, and 38 are illustrated in FIG. 1 as being co-located within a single processing unit, in embodiments in which processor 20 comprises multiple processing units, one or more of components 30, 32, and/or 38 may be located remotely from the other components. The description of the functionality provided by the different components 30, 32, and/or 38 described below is for illustrative purposes, and is not intended to be limiting, as any of components 30, 32, and/or 38 may provide more or less functionality than is described. For example, one or more of components 30, 32, and/or 38 may be eliminated, and some or all of its functionality may be provided by other components 30, 32, and/or 38. As another example, processor 20 may be configured to execute one or more additional components that may perform some or all of the functionality attributed below to one of components 30, 32, and/or 38.

Sleep parameter component 30 is configured to obtain and/or determine one or more sleep parameters related to sleep sessions of subject 12. The one or more sleep parameters may include and/or be related to SWA in subject 12, a sleep stage (e.g., N1, N2, N3), a sleep need, the power in the slow wave activity band (0.5-4.5 Hz) and/or other frequency bands of an EEG, and/or other parameters. In some embodiments, sleep parameter component 30 may be configured to generate an EEG, a hypnogram and/or other information based on the output signals from sensor 18, the obtained and/or determined parameters, and/or other information. In some embodiments, the EEG and/or the hypnogram may be used by sleep parameter component 30 to obtain and/or determine other parameters. The EEG and/or the hypnogram may be displayed, for example, by user interface 24.

Sleep parameter component 30 is configured to obtain an initial sleep need amount ($S_0$), a sleep need decay rate ($\gamma$), and/or other parameters for subject 12. The initial sleep need amount, the sleep need decay rate, and/or other obtained parameters may be previously determined (e.g., by sleep parameter component 30, by other components of system 10, and/or by other systems) based on information from one or more previous sleep sessions of subject 12 and/or other information. In some embodiments, obtaining the parameters may include retrieving parameters from electronic storage (e.g., electronic storage 22), for example. In some embodiments, the initial sleep need amount, the sleep need decay rate, and/or other parameters may be determined and/or adjusted (described below) during and/or based on one or more previous sleep sessions of subject 12 (e.g., a calibration phase) using EEG data and/or other data collected during at least one prior sleep session. In some embodiments, the initial sleep need amount, the sleep need decay rate, and/or other parameters may be default parameters (e.g., $S_0=1000$ $\mu V^2$, $\gamma=0.008$ $s^{-1}$).

Figure 3:
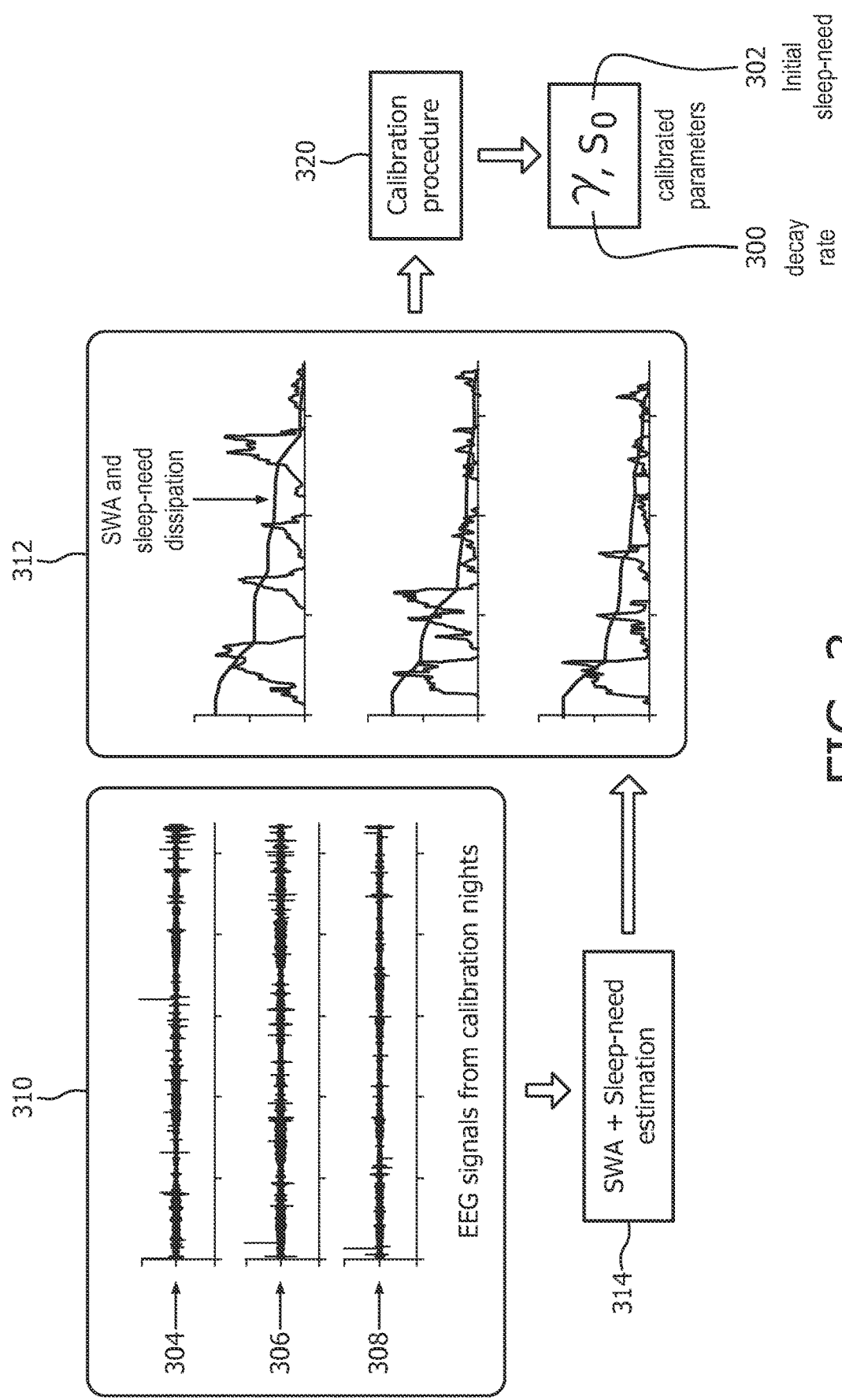
FIG. 3 illustrates determining a sleep need decay rate and an initial sleep need amount based on EEG signals for previous sleep sessions of the subject.

FIG. 3 illustrates determining 320 the sleep need decay rate ($\gamma$) 300 and the initial sleep need amount ($S_0$) 302 based on the EEG 310 for three previous sleep sessions (e.g., calibration nights) 304, 306, 308 of subject 12. In some embodiments, SWA and sleep need dissipation 312 are determined and/or estimated 314 (described below) based on the EEG signals from the three previous sleep sessions. However, FIG. 3 is not intended to be limiting. Although FIG. 3 illustrates determining the sleep need decay rate 300 and the initial sleep need amount 302 based on three previous sleep sessions, system 10 is configured to determine such parameters based on any number of previous sleep sessions of subject 12 on any number of days and/or nights, and/or other information.

In some embodiments, sleep parameter component 30 is configured to adjust the initial sleep need amount based on a wake time amount between an end of an immediately previous sleep session and a beginning of the target sleep session. Initial sleep need increases with the wake time amount between sleep sessions. Sometimes, subject 12 may stay awake for a significantly different (longer or shorter) period of time between sleep sessions relative to normal (e.g., the typical and/or average amount of time between sleep sessions that resulted in the obtained $S_0$ as described above). In these situations, system 10 is configured to adjust the initial sleep need amount ($S_0$) based on the actual duration of the wakeful time period. Such adjustment may be based on a sleep-need building model during wakefulness. This model indicates that sleep need dissipates exponentially during sleep and sleep need builds exponentially during wakefulness. In some embodiments, system 10 is configured to adjust the initial sleep need amount ($S_0$) based on Equation 1 and Equation 2 shown below, where t is the time from sleep onset in Equation 1 (e.g., t is 0 at sleep onset), t is the time counted from the wakeup moment in Equation 2, $\tau$ is a time constant characterizing the exponential fit (this parameter may be obtained via information from previous sleep sessions of subject 12), and $\Delta t$ is the difference (e.g., positive if the wakefulness duration is longer than typical/average or negative if the wakefulness duration is shorter than typical/average) in the wake time amount.

$$S(t) \approx S_0 \exp\left(-\frac{t}{\tau}\right), \quad \text{during sleep} \tag{1}$$

$$S(t) \approx S_0\left[1 - \exp\left(-\frac{2t}{\tau}\right)\right]. \quad \text{during wakefulness}$$

$$\Delta S = \frac{2S_0}{\tau} \exp\left(-\frac{2t}{\tau}\right)\Delta t, \tag{2}$$

Figure 4:
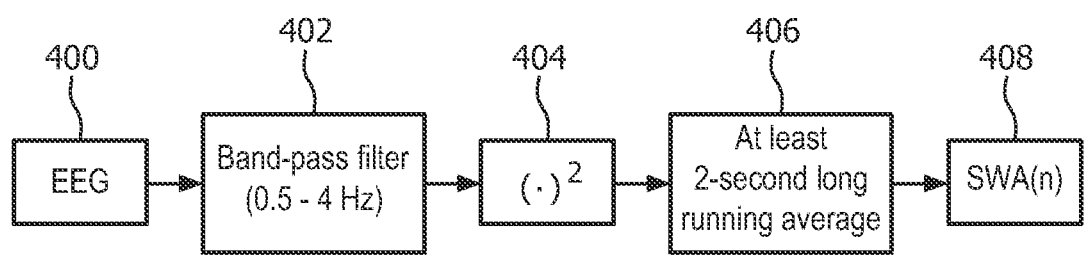
FIG. 4 illustrates slow wave activity estimation in real-time or near real-time.

In some embodiments, sleep parameter component 30 is configured to determine one or more sleep parameters based on the output signals from sensor 18 during the target sleep session and/or other information. In some embodiments, sleep parameter component 30 is configured to determine an amount of SWA in subject 12 during the target sleep session based on the output signals. In some embodiments, sleep parameter component 30 is configured to determine the amount of SWA in subject 12 in real-time and/or near real-time during the target sleep session. Sleep parameter component 30 may determine SWA in subject 12 based on an analysis of the information conveyed by the output signals of sensor 18. In some embodiments, determining the SWA may include estimating the SWA. Determining and/or estimating the SWA and/or other parameters may include generating and/or monitoring an EEG during a sleep session of subject 12. In some embodiments, SWA may be quantified by sleep parameter component 30 via the EEG spectral power in the about 0.5 to about 4.5 Hz frequency range, for example. In some embodiments, the SWA may be dynamically determined and/or estimated with a time resolution as high as the sampling rate by (1) applying a band-pass filter to the signal in the frequency band (e.g., about 0.5 to about 4.5 Hz), (2) taking the square root of the results, (3) taking the running average over a window of time with a typical duration (e.g., 2 seconds), and/or performing other operations. FIG. 4 illustrates SWA estimation 410 in real-time or near real-time. As described above, EEG data 400 is filtered 402 and then a square root is taken 404. A running average of these results is then determined 406 for a predetermined period of time (e.g., 2 seconds).

Returning to FIG. 1, sleep need dissipation component 32 is configured to determine a metric indicating sleep need dissipation in the subject during the target sleep session. The metric is determined based on the output signals from sensor 18, the initial sleep need amount, the sleep need decay rate, the determined amount of slow wave activity, and/or other information. In some embodiments, the metric may be related to the sleep need dissipation (e.g., a derivative of the sleep need dissipation and/or a final sleep need). In some embodiments, the metric may be the sleep need dissipation. In some embodiments, sleep need dissipation component 32 may determine an instantaneous sleep need one or more times during the sleep session (e.g., S(t)) based on the determined SWA. The metric indicating sleep need dissipation may be determined based on differences between two or more of the instantaneous sleep need determinations. In some embodiments, sleep need dissipation component 32 is configured to determine the sleep need dissipation metric based on a model that characterizes the relation between the SWA and the sleep need (S(t)) in subject 12. A model relating the dynamic variation of SWA to sleep need is described by Equation 3 below.

$$\frac{dS(t)}{dt} = -\gamma \cdot SWA(t) \quad (3)$$

In Equation 3, the instantaneous rate of decrease in sleep need is related to the SWA during NREM sleep by sleep need decay rate γ (obtained and/or determined as described above). In Equation 3, S(t) is the sleep need as a function of time. Taking the integral of both sides in Equation 3 from sleep onset "$t_0$" to an arbitrary time "t" yields Equation 4.

$$\int_{t_0}^{t} \frac{dS(t)}{dt} dt = -\gamma \cdot \int_{t_0}^{t} SWA(t)dt, \quad (4)$$

$$S(t) - S_0 = -\gamma \cdot CUMSWA(t),$$

$$CUMSWA(t) = \frac{S_0 - S(t)}{\gamma}$$

The summation of the SWA from sleep onset to a time "t" is referred to as cumulative SWA up to time "t" or, in short, CUMSWA(t). This can also be visualized as the area under the SWA curve (S(t) 208) in FIG. 2. The decrease in sleep need "$S_0 - S(t)$" up to time "t" is directly proportional to CUMSWA(t) (see Equation 4). Thus, CUMSWA(t) provides an indication of the restorative value of sleep up to time "t".

Using the obtained and/or determined (as described above) parameters $S_0$ and γ, sleep need dissipation component 32 determines and/or estimates (e.g., in real-time or near real-time) the sleep-need and/or sleep need dissipation for the target sleep session. This may be achieved by discretizing Equation 3 as follows:

$$\frac{dS(t)}{dt} = -\gamma \cdot SWA(t), \quad (5)$$

$$S(n) - S(n-1) = -\gamma SWA(n),$$

$$S(n) = S(n-1) - \gamma SWA(n).$$

In Equation 5, "n" is the discrete version of time. The SWA may be dynamically determined/estimated as described above. The sleep need at time "n", may then (according to Equation 3) be calculated in a recursive manner using the sleep-need at time "n−1", the decay rate, and the SWA at time n.

In some embodiments, system 10 may be configured such that the SWA in periods outside NREM sleep is assumed to be zero. While the SWA is typically low in REM and during wakefulness, noisy segments in these states may introduce outliers to the SWA determination/estimation. Noisy periods from the EEG may be detected by applying a threshold on the high frequency (e.g., alpha from 8 to 12 Hz, beta from 15 to 30 Hz) content of the EEG and excluding information that breaches the threshold. Having detected the noisy periods, their corresponding SWA may be set to zero so they do not contribute to the sleep-need dissipation determination. Alternatively and/or in addition, system 10 may be configured such that a real-time sleep stage detection algorithm may be applied to detect EEG segments corresponding to sleep stages other than N2 or N3. The SWA associated with these segments may be set to zero so they do not contribute to the sleep-need dissipation determination.

Using information (e.g., output signals generated by sensor 18, EEG data, parameters obtained by parameter component 30, parameters determined by parameter component 30, the sleep need dissipation metric determined by sleep need dissipation component 32, and/or other information) from one or more sleep sessions (e.g., calibration nights and/or the target sleep session), the parameters $S_0$ and γ may be customized for subject 12 and/or other users by sleep parameter component 30, sleep need dissipation component 32, and/or other components of system 10. For example, the discretized Equation (5) is valid from n=0 to n=N−1, where N is the discrete time corresponding to the wake-up time (e.g., counter from sleep onset). For example, if the wake-up time is 6 hours, and the sampling frequency is 100 samples-per second, then N=2160000. This implies:

$$S(n-1) = S(n) + \gamma SWA(n), \text{ for } n=0, \ldots, N-1. \quad (6)$$

The final sleep need (e.g., at the end of a given sleep session) is equal to the final value of SWA (Equation 7).

$$S(N-1) = SWA(N-1) \quad (7)$$

In addition, the sleep need and the SWA at the time in the first sleep cycle where the SWA is at and/or near its maximum are substantially equal. This is implied by Equation 8 (where $r_c$ is a constant that does not equal zero).

$$\frac{dSWA(t)}{dt} = r_c SWA(t) \left[1 - \frac{SWA(t)}{S(t)}\right], \quad (8)$$

When SWA(t) reaches a local maximum, then dSWA(t)/d(t)= 0. This implies that the sleep need is substantially equal to the SWA. In the discrete time notation, this gives:

$$n_{MAX} = \underset{n \in \text{First cycle}}{\arg\max} \{SWA(n)\}, \quad (9)$$

$$S(n_{MAX}) = SWA(n_{MAX}).$$

Using Equations 6, 7, and 9:

$$S(n_{MAX}) = S(N-1) + \gamma \sum_{n=n_{MAX}+1}^{N-1} SWA(n). \quad (10)$$

The formula to estimate the decay-rate $\gamma$ may then be derived as shown in Equation 11.

$$\gamma = \frac{S(n_{MAX}) - S(N-1)}{\sum_{n=n_{MAX}+1}^{N-1} SWA(n)}, \quad (11)$$

$$\gamma = \frac{SWA(n_{MAX}) - SWA(N-1)}{\sum_{n=n_{MAX}+1}^{N-1} SWA(n)}.$$

Using the decay-rate estimate in Equation 10, the initial sleep-need may be directly obtained from Equation 6.

$$S_0 = \gamma \sum_{n=0}^{N-1} SWA(n) + SWA(N-1). \quad (12)$$

Figure 5:
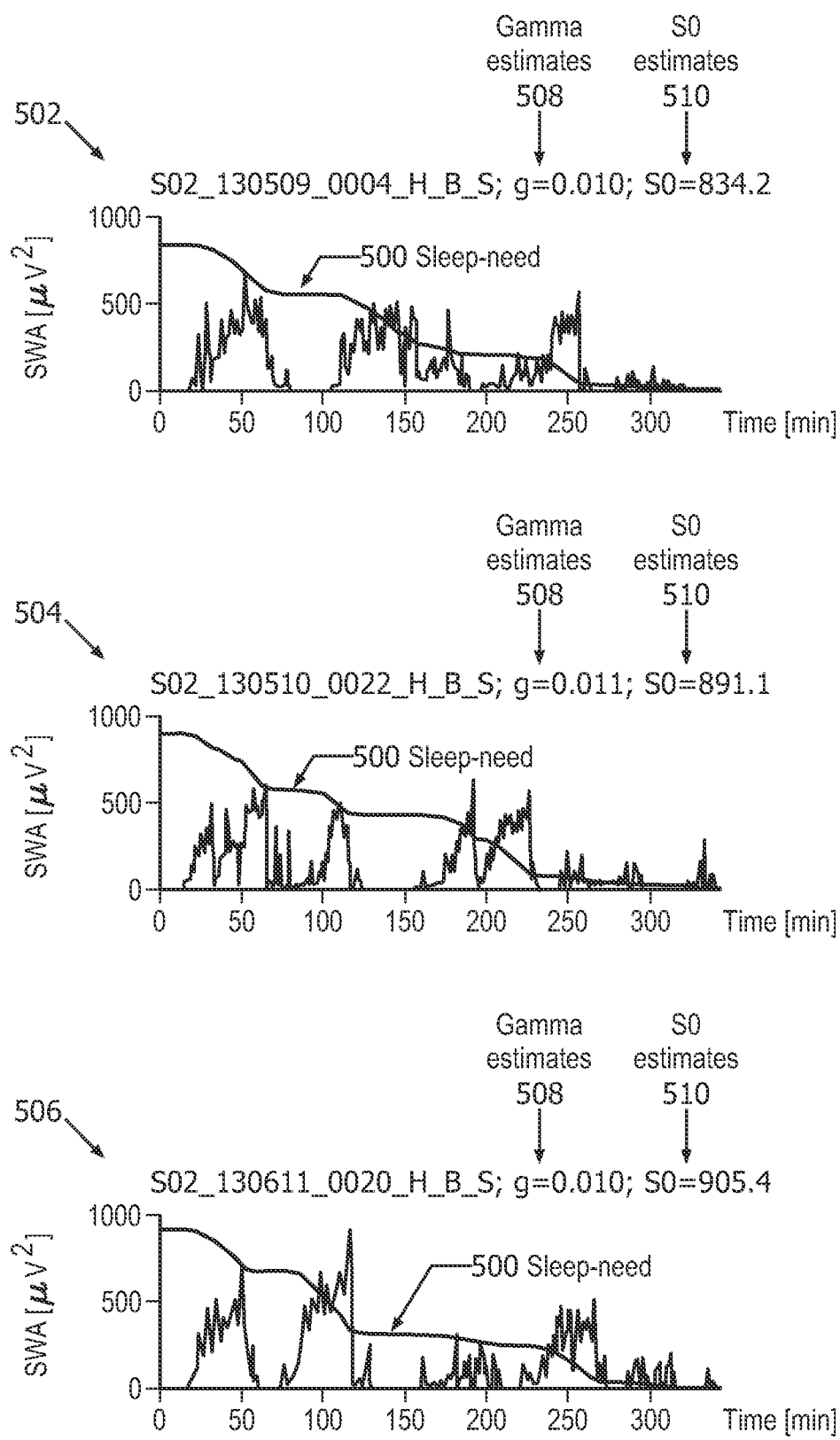
FIG. 5 illustrates an example of a sleep need determination/estimation.

An example of the sleep need determination/estimation 500 is shown in FIG. 5 for three different overnight datasets 502, 504, 506 (e.g., generated based on the output signals from sensor 18) for the same subject (e.g., subject 12). The values of the decay rate 508 and the initial sleep need 510 are indicated for the individual nights. The decay rate and initial sleep need for different nights are relatively close in value to each other. In some embodiments, the estimates for individual nights may be averaged. For the particular example in FIG. 5, the averages are: $\gamma=0.0102$ s$^{-1}$ and $S_0=876.93$ $\mu V^2$.

Returning to FIG. 1, control component 38 is configured to cause user interface 24 and/or other user interfaces to graphically display the sleep restoration level of subject 12 for the target sleep session. In some embodiments, the sleep restoration level comprises a visual representation of the metric indicating sleep need dissipation.

In some embodiments, control component 38 is configured such that causing user interface 24 to graphically display the sleep restoration level of subject 12 for the target sleep session includes causing user interface 24 to display the metric indicating sleep need dissipation and/or other parameters related to the sleep need dissipation in polar co-ordinates on a homeostatic clock. As described above, having obtained the decay rate and initial sleep need that were determined based on one or more previous sleep sessions (e.g., calibration nights), the sleep need may be determined one or more times during any arbitrary night of sleep of the same subject (subject 12) for which EEG data (e.g., information from sensor 18 that is used to determine SWA) is available. In some embodiments, control component 38 is configured to map S(n) (described above) to a (homeostatic) clock representation. In these embodiments, control component 38 is configured to represent S(n) in a polar coordinate system where n may be assumed to represent, for example, a 30 second long epoch index, and is related to the angle (in radians) as:

$$\phi(n) = \frac{\pi}{2} - n\frac{\pi}{720} \quad (13)$$

where the radius is S(n), and 2(n) represents the number of minutes (for example) since sleep onset. For example, the sleep need one hour into the sleep session (e.g., after starting EEG monitoring) is S(120) and the angle (in radians) is π/3 or 60°, for example.

Figure 6A:
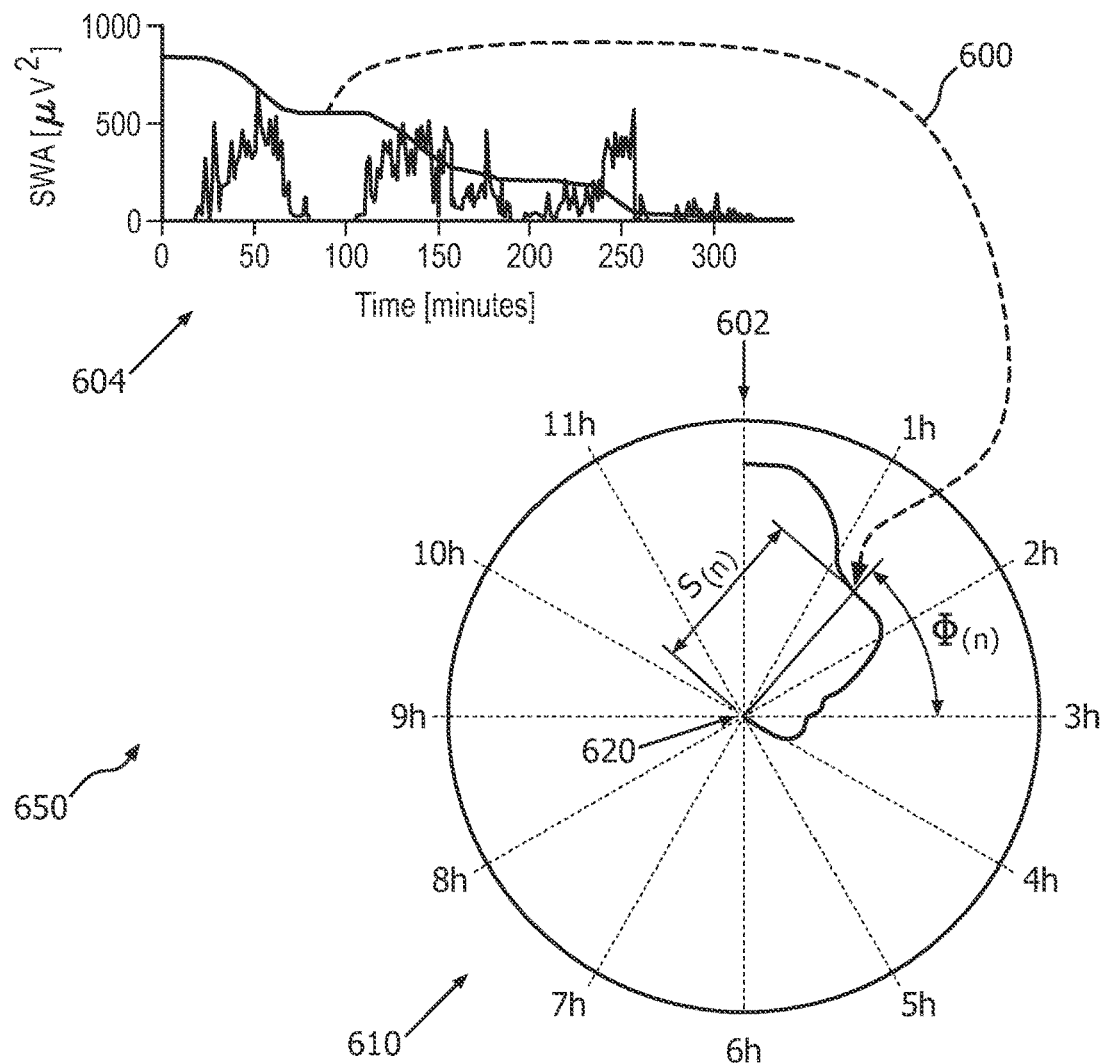
FIG. 6A illustrates an example of SWA over time 604 and the corresponding decreasing sleep need.
Figure 6B:
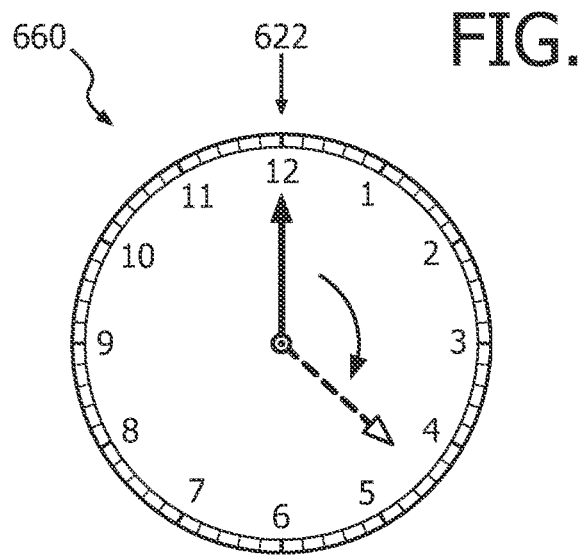
FIG. 6B illustrates an example of a graphical clock representation of sleep need dissipation.

FIG. 6A illustrates an example of a graphical representation 650 of the sleep need dissipation determined as described above, which illustrates SWA over time 604 and the corresponding decreasing sleep need S(n) 600. In FIG. 6A, S(n) 600 is mapped to an image of a homeostatic clock 610. In this example, the subject entered bed at midnight 602 and sleep need S(n) was fully dissipated after four hours 620. Using such a clock-like representation, it may be possible to shift the sleep need 600 curve between various sleep session start times (e.g., rotate the whole curve clockwise and/or counter clockwise from midnight) and predict when the subject is likely to be fully restored (e.g., the sleep need has decreased to zero). Such a representation facilitates determining whether entering bed earlier or later has an influence on sleep-need dissipation (e.g., does the sleep need dissipate at the same rate as a previous night independent of sleep session start time or not, is sleep need fully dissipated after the same amount of time, etc.). In some embodiments, as shown in FIG. 6B, the information communicated by the example in FIG. 6A may be illustrated on a traditional clock 660. In this example, the clock may indicate that if the subject goes to bed at midnight 662, his or her sleep need is fully dissipated by 4 AM.

In some embodiments, control component 38 is configured such that the graphical display of the sleep restoration level comprises a multi-colored battery level indicator and/or traffic light indicator having a red colored portion that indicates a high sleep need and a green colored portion that indicates a low sleep need, and/or other graphical display indicators.

Figure 7:
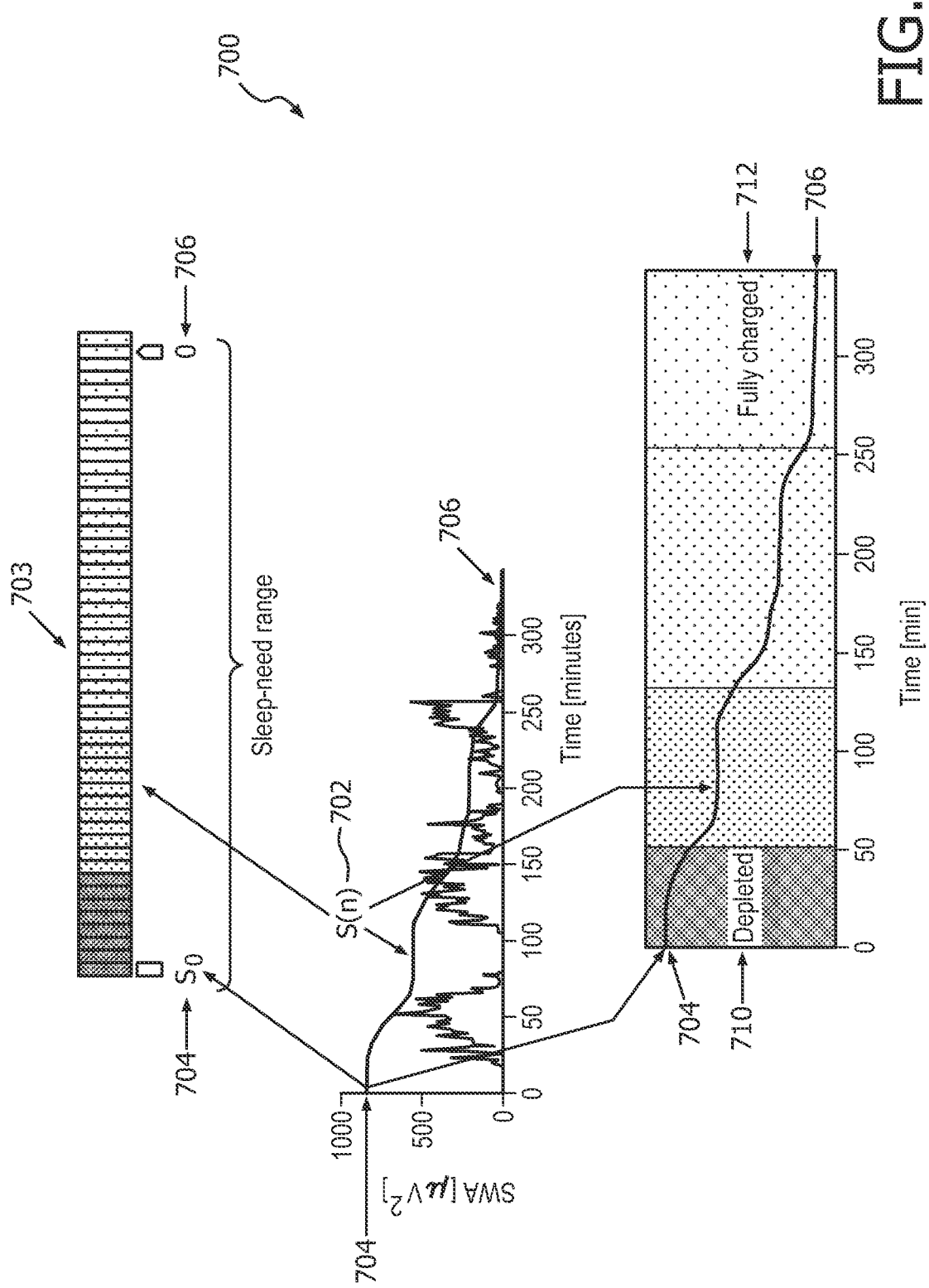
FIG. 7 illustrates an example of a multi-colored battery level sleep need indicator.

For example, FIG. 7 illustrates one possible version of a multi-colored battery level sleep need indicator 700. In FIG. 7, the values of S(n) 702 are mapped into a color scale 703 which spans from red (corresponding to $S_0$ 704) conveying the notion of being "depleted" 710 to green (corresponding to $S_{final}$ 706) and conveying the notion of being "fully charged" 712. In some embodiments, $S_0$ 704 and is determined as described above based on one or more previous sleep sessions of subject 12 (e.g., calibration nights), the target sleep session of subject 12, and/or other information.

Figure 8:
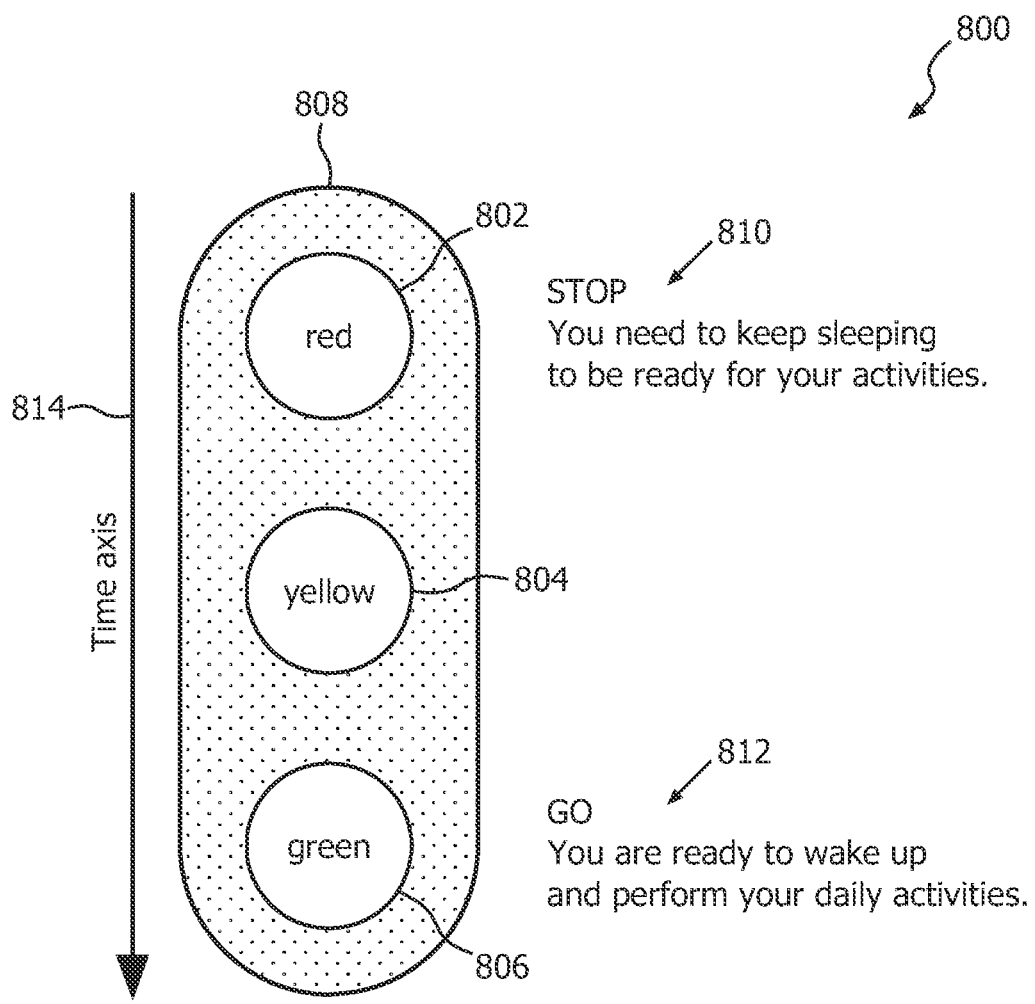
FIG. 8 illustrates an example of a multi-colored traffic light sleep need indicator.

FIG. 8 illustrates one possible version of a multi-colored traffic light sleep need indicator 800. In FIG. 8, the values of S(n) and $S_{final}$ are mapped onto a red 802, yellow 804, and green 806 traffic light 808. This indicator relates the cues associated with stopping and moving a car to staying in bed 810 and getting out of bed 812. As a sleep session progresses 814 and sleep need dissipates in subject 12 (FIG. 1), the indicator changes from red 802, to yellow 804, to green 806. The transitions between colors may correspond to predetermined points on the sleep need curve S(n) (e.g., S(n) 702 shown in FIG. 7), cumulative amounts of sleep need dissipation, and/or other thresholds that may be determined at manufacture, may be determined by subject 12 and/or other users, may be determined based on previous sleep sessions of subject 12 and/or be determined in other ways.

Figure 9:
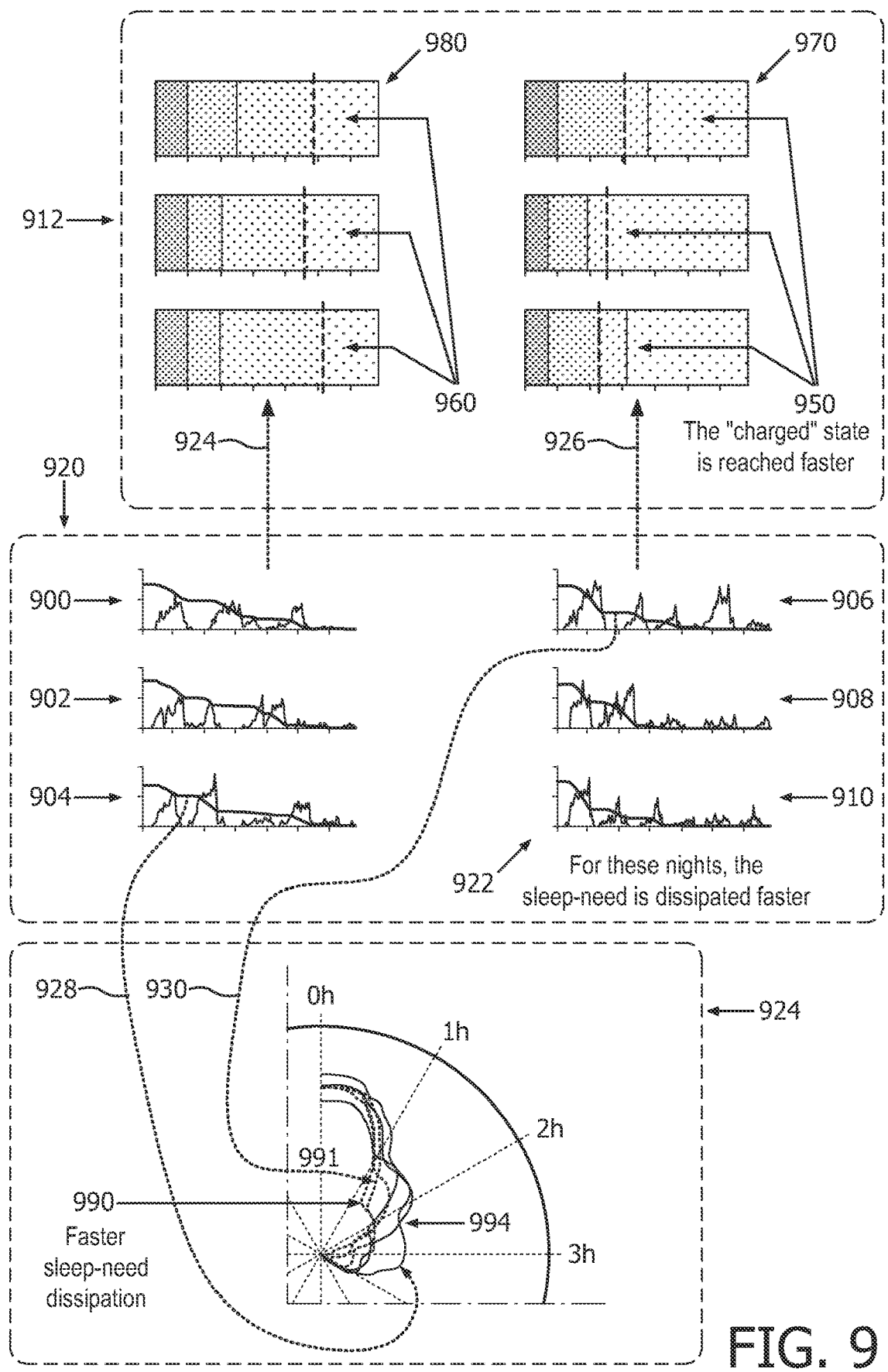
FIG. 9 illustrates a comparison of sleep need dissipation during six individual sleep sessions.

In some embodiments, system 10 is configured to facilitate a comparison of sleep need dissipation over two of more sleep sessions (e.g, nights) of the same subject (subject 12). This may allow a user and/or a physician, for example, to compare and test different strategies to improve sleep need dissipation. FIG. 9 illustrates a comparison of sleep need dissipation during six individual sleep sessions 900, 902, 904, 906, 908, 910. In FIG. 9, sleep sessions 900, 902, and 904 are baseline nights of sleep. Sensory stimulation (e.g., auditory tones) was provided to the subject during sleep sessions 906, 908, and 910. The six sleep sessions are compared using multicolored battery level indicators 912 and the clock representation 914 described above.

The plots of SWA over time 920 are mapped 924, 926 to the multicolored battery level indicators 912 and mapped 928, 930 to clock representation 914. The plots of SWA over time 920, illustrate that sleep need is dissipated faster 922 during sleep sessions 906, 908, and 910. This is also clear in the multicolored battery level indicators 912 because the charged state 950 is reached sooner for the battery level indicators 970 that map to sleep sessions 906, 908, and 910 (e.g., the charged state is reached in less than about 250 minutes) than the charged state 960 for the battery level indicators 980 that map to sleep sessions 900, 902, and 904. In clock representation 914, the lines 991 representing sleep need that map to sleep sessions 906, 908, and 910 reach the center 992 of clock representation 914 sooner 990 than the lines 994 that map to sleep sessions 900, 902, and 904. System 10 is configured such that the same and/or similar comparisons may be done with the traffic light sleep need indicator (described above). For example, a smaller traffic light may represent more effective sleep dissipation. A bigger traffic light may represent less effective sleep dissipation.

Figure 10:
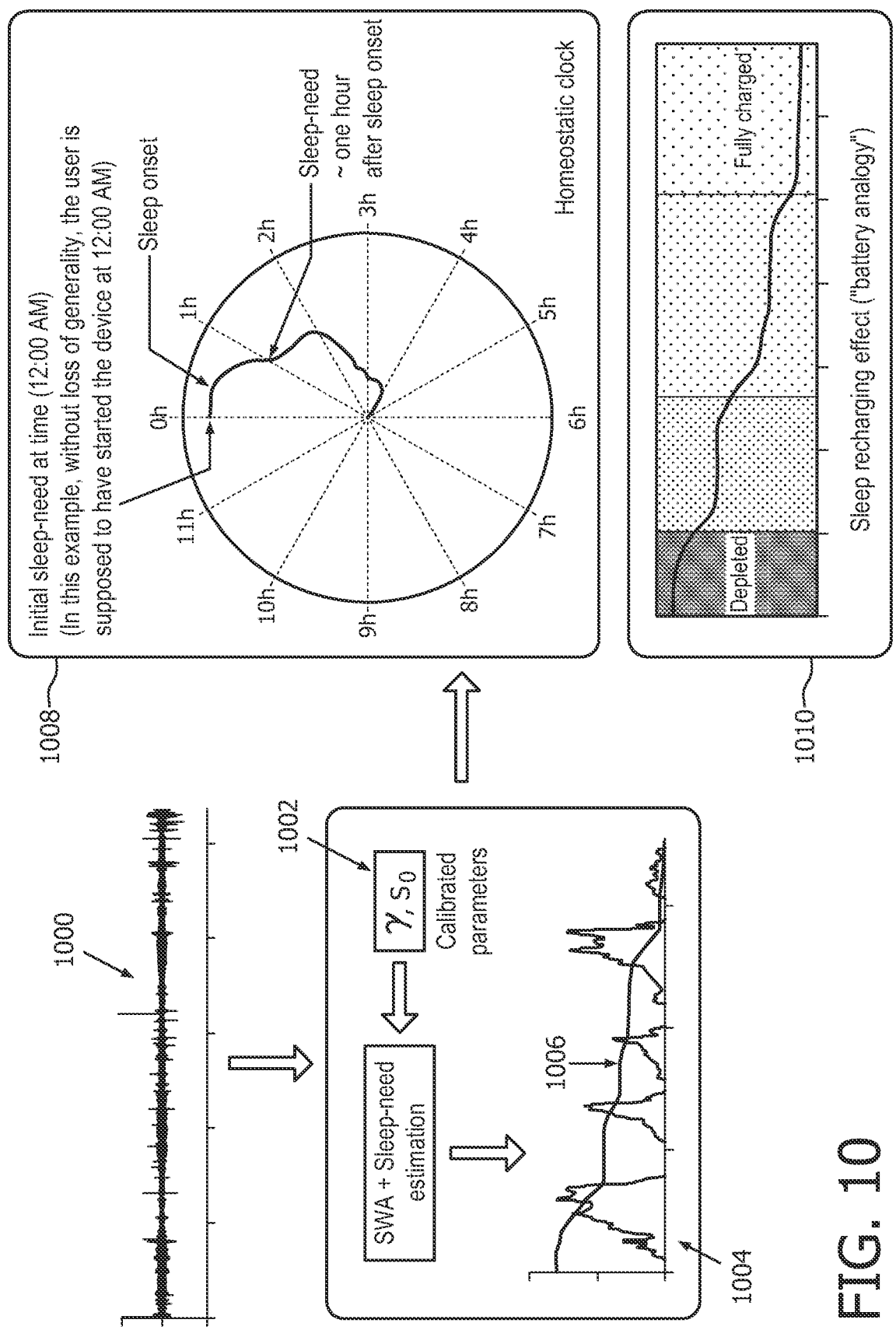
FIG. 10 is a non-limiting summary of the operations performed by the system.

FIG. 10 is a non-limiting summary of the operations performed by system 10. FIG. 10 illustrates generating output signals 1000 conveying information related to SWA in a subject (e.g., subject 12 shown in FIG. 1), obtaining 1002 an initial sleep need and a sleep need decay rate that were determined based on one or more previous sleep sessions of the subject, determining 1004 an amount of slow wave activity in the subject during the target sleep session based on the output signals and a metric indicating sleep need dissipation 1006 in the subject during the target sleep session, and causing a user interface to graphically display 1008, 1010 the sleep restoration level of the subject for the target sleep session. FIG. 10 illustrates a graphical display of both a clock representation 1008 and a multicolored battery level indicator 1010.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensor 18, processor 20, electronic storage 22, and/or other components of system 10. For example, an EEG may be displayed to a caregiver via user interface 24. As another example, control component 38 may cause user interface 24 to graphically display the sleep restoration level of the subject for the target sleep session (as described above).

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensor 18, processor 20, electronic storage 22, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 11:
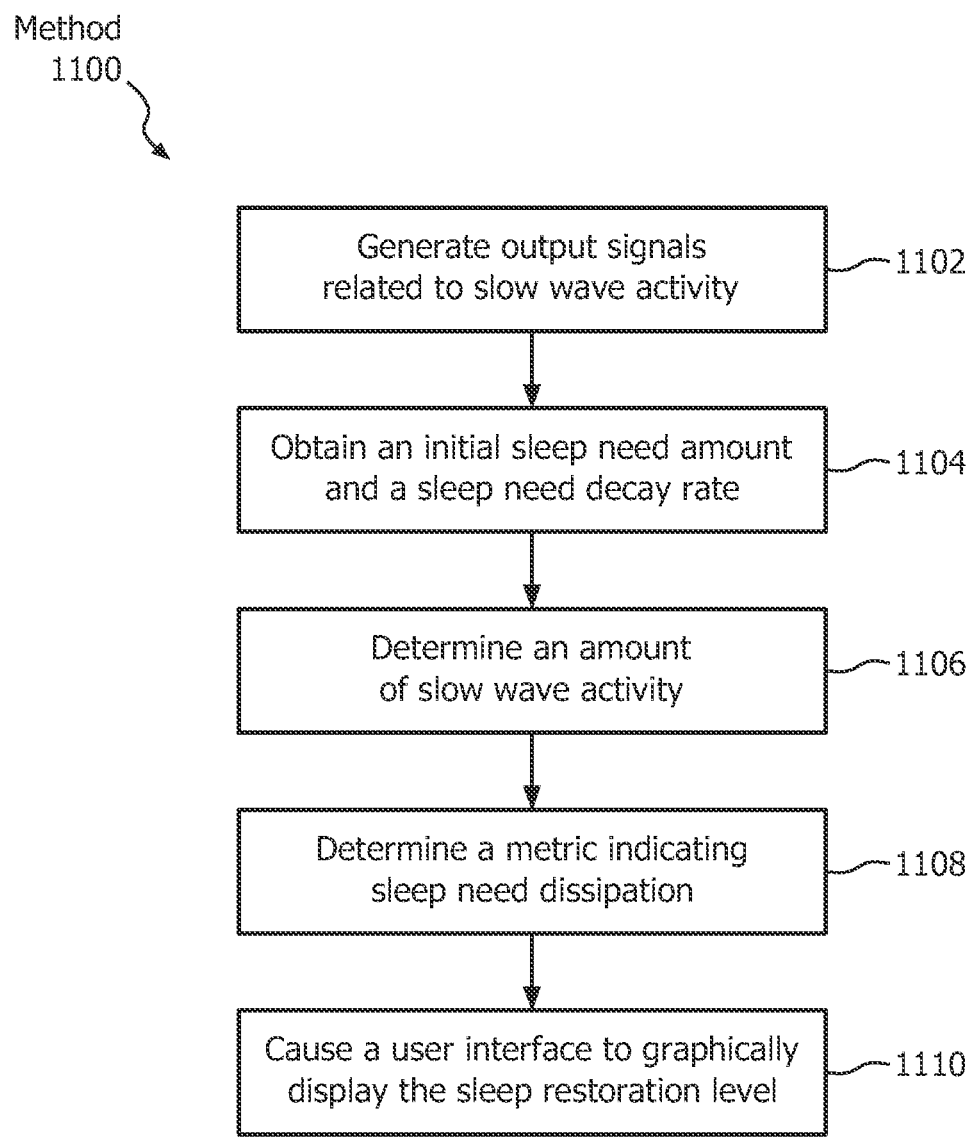
FIG. 11 illustrates a method for determining and displaying a sleep restoration level of a subject for a target sleep session with a determination system.

FIG. 11 illustrates a method 1100 for determining and displaying a sleep restoration level of a subject for a target sleep session with a determination system. The determination system comprises one or more sensors, one or more physical computer processors, and/or other components. The one or more physical computer processors are configured to execute computer program components. The computer program components comprise a sleep parameter component, a sleep pressure dissipation component, a control component, and/or other components. The operations of method 1100 presented below are intended to be illustrative. In some embodiments, method 1100 may be accomplished with one or more additional operations not described, and/or without one or more of the operations discussed. Additionally, the order in which the operations of method 1100 are illustrated in FIG. 11 and described below is not intended to be limiting.

In some embodiments, method 1100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1100 in response to instructions stored electronically on an electronic storage medium. The one or more processing devices may include one or more devices configured through hardware, firmware, and/or software to be specifically designed for execution of one or more of the operations of method 1100.

At an operation 1102, output signals conveying information related to slow wave activity in the subject during the target sleep session are generated. In some embodiments, operation 1102 is performed by one or more sensors the same as or similar to sensors 18 (shown in FIG. 1 and described herein).

At an operation 1104, an initial sleep need amount, a sleep need decay rate, and/or other parameters are obtained. In some embodiments, the initial sleep need amount, the sleep need decay rate, and/or other parameters are determined based on the output signals. In some embodiments, the initial sleep need amount may be adjusted based on a wake time amount between an end of an immediately previous sleep session and a beginning of the target sleep session, and/or other information. In some embodiments, operation 1104 is performed by a computer program component the same as or similar to sleep parameter component 30 (shown in FIG. 1 and described herein).

At an operation 1106, an amount of slow wave activity in the subject is determined. In some embodiments, the amount of slow wave activity in the subject is determined in real-time or near real-time during the sleep session. In some embodiments, operation 1106 is performed by a computer program component the same as or similar to sleep parameter component 30 (shown in FIG. 1 and described herein).

At an operation 1108, a metric indicating sleep need dissipation is determined. The metric indicates sleep need dissipation in the subject during the target sleep session. The metric is determined based on the initial sleep need amount, the sleep need decay rate, the determined amount of slow wave activity, and/or other parameters. In some embodiments, operation 1108 is performed by a computer program component the same as or similar to sleep need dissipation component 32 (shown in FIG. 1 and described herein).

At an operation 1110, a user interface is caused to graphically display the sleep restoration level of the subject for the target sleep session. In some embodiments, the sleep restoration level comprises a visual representation of the metric indicating sleep need dissipation. In some embodiments, causing the user interface to graphically display the sleep restoration level of the subject for the target sleep session includes causing the user interface to display the metric indicating sleep need dissipation in polar co-ordinates on a homeostatic clock. In some embodiments, the graphical display of the sleep restoration level comprises a multi-colored battery level indicator and/or a traffic signal indicator having a red colored portion that indicates a high sleep need and a green colored portion that indicates a low sleep need. In some embodiments, operation 1110 is performed by a computer program component the same as or similar to control component 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine and display a sleep restoration level of a subject for a target sleep session, the system comprising:
   one or more sensors configured to generate output signals conveying information related to slow wave activity in the subject during the target sleep session; and
   one or more physical computer processors configured by computer readable instructions to:
   obtain an initial sleep need amount and a sleep need decay rate determined based on information from one or more previous sleep sessions of the subject, wherein the sleep need decay rate is a rate of decrease in sleep need during a sleep session;
   adjust the initial sleep need amount based on a wake time amount between an end of an immediately previous sleep session and a beginning of the target sleep session;
   determine an amount of slow wave activity in the subject during the target sleep session based on the output signals;
   determine a metric indicating sleep need dissipation in the subject during the target sleep session, wherein the sleep need dissipation is a decrease in sleep need while the subject is sleeping during the target session, the metric determined based on the adjusted initial sleep need amount, the sleep need decay rate, and the determined amount of slow wave activity; and cause a user interface to graphically display the sleep restoration level of the subject for the target sleep session, the sleep restoration level comprising a visual representation of the metric indicating sleep need dissipation.

2. The system of claim 1, wherein the one or more physical computer processors are configured to determine the amount of slow wave activity in the subject in real-time during the target sleep session.

3. The system of claim 1, wherein the one or more physical computer processors are configured such that causing the user interface to graphically display the sleep restoration level of the subject for the target sleep session includes causing the user interface to display the metric indicating sleep need dissipation in polar co-ordinates on a homeostatic clock.

4. The system of claim 1, wherein the one or more physical computer processors are configured such that the graphical display of the sleep restoration level comprises a multi-colored battery level indicator having a red colored portion that indicates a high sleep need and/or a low amount of sleep need dissipation and a green colored portion that indicates a low sleep need and/or a high amount of sleep need dissipation.

5. A method for determining and displaying a sleep restoration level of a subject for a target sleep session with a determination system, the determination system comprising one or more sensors, and one or more physical computer processors, the method comprising:

generating, with the one or more sensors, output signals conveying information related to slow wave activity in the subject during the target sleep session;

obtaining, with the one or more physical computer processors, an initial sleep need amount and a sleep need decay rate determined based on information from one or more previous sleep sessions of the subject, wherein the sleep need decay rate is a rate of decrease in sleep need during a sleep session;

adjusting, with the one or more processors, the initial sleep need amount based on a wake time amount between an end of an immediately previous sleep session and a beginning of the target sleep session;

determining, with the one or more physical computer processors, an amount of slow wave activity in the subject during the target sleep session based on the output signals;

determining, with the one or more physical computer processors, a metric indicating sleep need dissipation in the subject during the target sleep session, wherein the sleep need dissipation is a decrease in sleep need while the subject is sleeping during the target session, the metric determined based on the adjusted initial sleep need amount, the sleep need decay rate, and the determined amount of slow wave activity; and causing, with the one or more physical computer processors, a user interface to graphically display the sleep restoration level of the subject for the target sleep session, the sleep restoration level comprising a visual representation of the metric indicating sleep need dissipation.

6. The method of claim 5, further comprising determining, with the one or more physical computer processors, the amount of slow wave activity in the subject in real-time during the target sleep session.

7. The method of claim 5, wherein causing the user interface to graphically display the sleep restoration level of the subject for the target sleep session includes causing the user interface to display the metric indicating sleep need dissipation in polar co-ordinates on a homeostatic clock.

8. The method of claim 5, wherein the graphical display of the sleep restoration level comprises a multi-colored battery level indicator having a red colored portion that indicates a high sleep need and/or a low amount of sleep need dissipation and a green colored portion that indicates a low sleep need and/or a high amount of sleep need dissipation.

9. A system configured to determine and display a sleep restoration level of a subject for a target sleep session, the system comprising:

means for generating output signals conveying information related to slow wave activity in the subject during the target sleep session;

means for obtaining an initial sleep need amount and a sleep need decay rate determined based on information from one or more previous sleep sessions of the subject wherein the sleep need decay rate is a rate of decrease in sleep need during a sleep session;

means for adjusting the initial sleep need amount based on a wake time amount between an end of an immediately previous sleep session and a beginning of the target sleep session;

means for determining an amount of slow wave activity in the subject during the target sleep session based on the output signals;

means for determining a metric indicating sleep need dissipation in the subject during the target sleep session, wherein the sleep need dissipation is a decrease in sleep need while the subject is sleeping during the target session, the metric determined based on the adjusted initial sleep need amount, the sleep need decay rate, and the determined amount of slow wave activity; and means for causing a user interface to graphically display the sleep restoration level of the subject for the target sleep session, the sleep restoration level comprising a visual representation of the metric indicating sleep need dissipation.

10. The system of claim 9, wherein the means for determining an amount of slow wave activity is configured to determine the amount of slow wave activity in the subject in real-time during the target sleep session.

11. The system of claim 9, wherein the means for causing is configured such that causing the user interface to graphically display the sleep restoration level of the subject for the target sleep session includes causing the user interface to display the metric indicating sleep need dissipation in polar co-ordinates on a homeostatic clock.

12. The system of claim 9, wherein the means for causing is configured such that the graphical display of the sleep restoration level comprises a multi-colored battery level indicator having a red colored portion that indicates a high sleep need and/or a low amount of sleep need dissipation and a green colored portion that indicates a low sleep need and/or a high amount of sleep need dissipation.

* * * * *